United States Patent

Stock

[11] Patent Number: 6,096,558
[45] Date of Patent: Aug. 1, 2000

[54] PROCESS FOR CALIBRATING A BREATH ALCOHOL-MEASURING INSTRUMENT

[75] Inventor: Burkhard Stock, Lübeck, Germany

[73] Assignee: Dräger Sicherheitstechnik GmbH, Lübeck, Germany

[21] Appl. No.: 09/022,246

[22] Filed: Feb. 11, 1998

[30] Foreign Application Priority Data

Sep. 13, 1997 [DE] Germany .......................... 197 40 342

[51] Int. Cl.$^7$ .................................................. G01N 33/00
[52] U.S. Cl. .......................... 436/132; 436/55; 436/150; 436/900; 422/84; 422/105; 422/98; 73/23.3
[58] Field of Search .................................. 436/2, 8, 9, 55, 436/132, 149, 150, 900; 73/23.3; 422/84, 98, 105

[56] References Cited

U.S. PATENT DOCUMENTS

| 4,003,240 | 1/1977 | Durbin | 73/23.41 |
|---|---|---|---|
| 4,278,636 | 7/1981 | Voigt et al. | 422/84 |
| 5,091,155 | 2/1992 | Takayama et al. | 436/900 |

FOREIGN PATENT DOCUMENTS

| 30 42 670 A1 | 10/1981 | Germany . | |
|---|---|---|---|
| 32 16 109 C2 | 11/1983 | Germany . | |
| 34 37 445 A1 | 5/1986 | Germany . | |
| 35 46 409 A1 | 7/1987 | Germany . | |
| 38 19 128 C2 | 12/1989 | Germany . | |
| 3-96844 | 4/1991 | Japan | 436/132 |

OTHER PUBLICATIONS

Yokogawa Electric Corp., Jul. 14, 1995, Gas Measuring Apparatus, *Patent Abstracts of Japan*.

Primary Examiner—Theresa T. Snider
Attorney, Agent, or Firm—McGlew and Tuttle, P.C.

[57] ABSTRACT

A process for calibrating a breath alcohol-measuring instrument (7) with a calibrating gas generator (1) with a liquid container (2) for aqueous ethanol solution and air feed device, which allow air to bubble through the ethanol solution and for passing gas from the atmosphere above the ethanol solution to the breath alcohol-measuring instrument (7). To equalize the temperature dependence of the ethanol concentration in the gas phase, without having to perform thermostatting, the process is applied with the following steps: Measurement of the temperature of the ethanol solution by means of a thermometer (8) and generation of an electric signal representing the temperature; reception of the electric signal in the transmission device (9) and passing on the electric signal or a signal processed from same to the breath alcohol-measuring instrument (7) and into its electronic evaluating unit; automatic conversion of the measurement result of the breath alcohol-measuring instrument (7) in the electronic evaluation unit into the measurement result to be expected at a preset reference temperature by means of a preset dependence on the temperature of the aqueous ethanol solution, which is obtained from the electric signal or from the processed signal, and on the preset reference temperature, and evaluation of the measurement result expected at the preset reference temperature for calibrating the breath alcohol-measuring instrument (7).

14 Claims, 1 Drawing Sheet

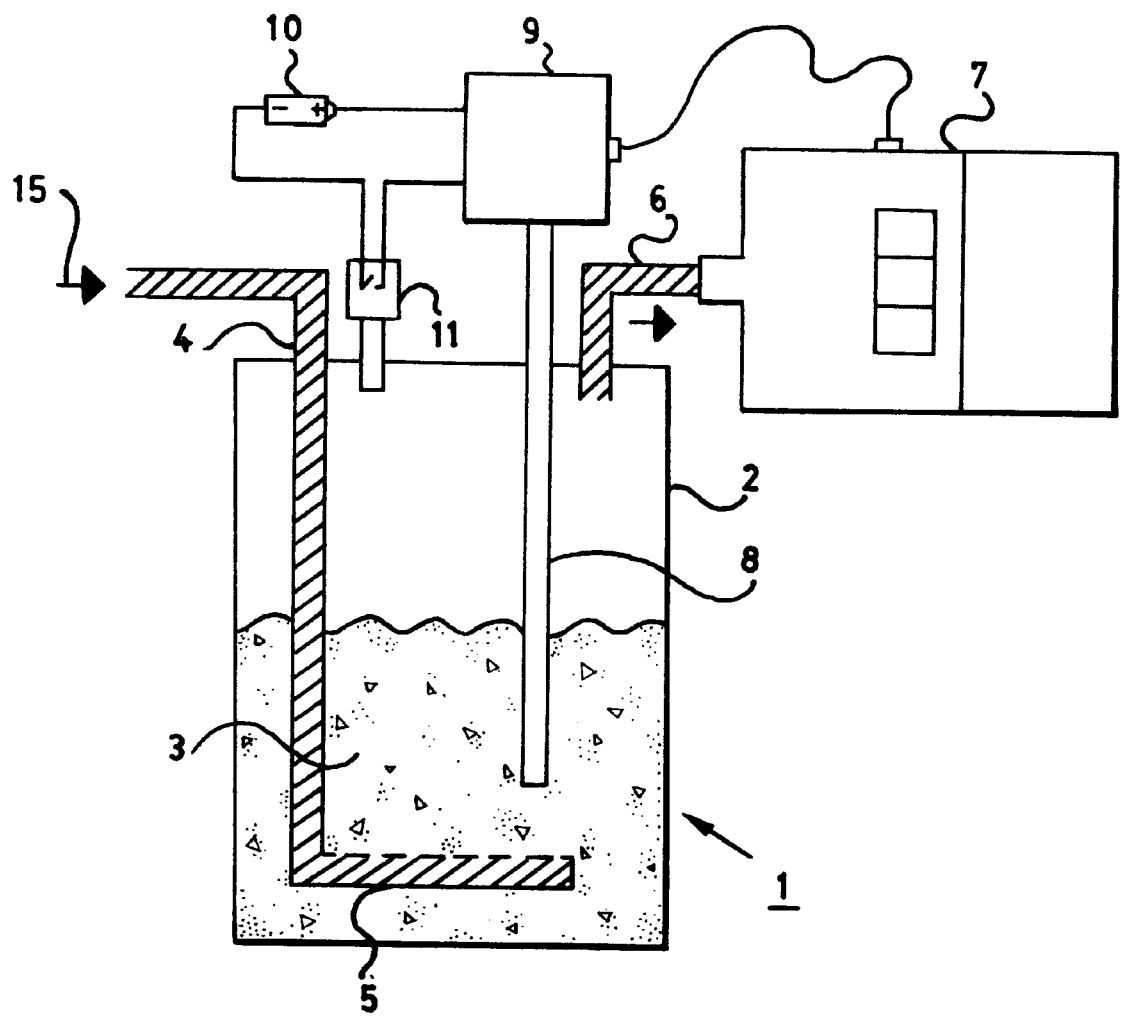

PROCESS FOR CALIBRATING A BREATH ALCOHOL-MEASURING INSTRUMENT

FIELD OF THE INVENTION

The present invention pertains to a process for calibrating a breath alcohol-measuring instrument by means of a calibrating gas generator with a liquid container for an aqueous ethanol solution and air feed means, which is designed for allowing air to bubble through the ethanol solution and for passing gas from the atmosphere above the ethanol solution to the breath alcohol-measuring instrument.

BACKGROUND OF THE INVENTION

Breath alcohol-measuring instruments have been increasingly used by police for checks in road traffic. To ensure the accuracy of measurement, especially with respect to subsequent legal proceedings, the breath alcohol-measuring instruments are calibrated at regular intervals. For calibration, it is necessary to provide a gas with a known ethanol concentration. Calibrating gas generators as they are described in, e.g., DE 32 16 109 C2 have been known for providing the test gas.

Prior-art calibrating gas generators have liquid containers which are filled with aqueous ethanol solutions of a known concentration. There also is provided air feed means, which draw in air by means of a pump and allows the air to escape in the liquid container, so that it bubbles through the ethanol solution. A line leads to the breath alcohol-measuring instrument from the gas atmosphere above the ethanol solution. While the air stream is bubbling through the solution in the form of fine bubbles, the air becomes enriched with ethanol and it becomes saturated with water vapor at the same time. The ethanol content in the air drawn off depends, according to Henry's law, on the concentration of ethanol in the ethanol solution and the temperature at which the ethanol is released from the liquid into the air.

The temperature dependence of the distribution coefficient $K_{a/W}$, which indicates the ratio of the alcohol concentration in the air relative to that in the water, can be described by the following temperature dependence:

$$K_{a/W} = 0.04145 \cdot e^{a \cdot T}$$

in which T is the temperature in °C. and a=0.0658 (1/°C.). This temperature dependence is described in, e.g., the article AtemalkoholmeBgeräte: Grundlagen der Kalibrierung [Breath Alcohol-measuring Instruments: Fundamentals of Calibration] by Günter Schoknecht and Bruno Barduhn, *Blutalkohol*, Vol. 32/1995, pp. 1–9.

It follows from the dependence described above that the temperature of the solution must be maintained at a constant value with the smallest possible deviation in order to obtain the most stable ethanol concentration possible in the gas phase. If, e.g., a relative stability of 1% of the ethanol concentration in the gas phase is sought, the temperature must be maintained at a constant value within a range of $\Delta T=0.01/a=0.15°$ C.

To bring the temperature to a preset reference value, the prior-art calibrating gas generators were provided with thermostat and heating means in order to bring the aqueous ethanol solution to a reference temperature of 34° C. and to carry out the calibration at this reference temperature. It was thus possible to perform the calibration at a preset, fixed reference temperature and known ethanol concentration in the aqueous solution.

The drawback of the prior-art procedure is that a mobile use of the calibration process is possible to a very limited extent only, because the heating means for the calibrating gas generators require an energy supply. Another drawback is a relatively long heat-up time required to bring the system into a stable, heated-up state. Condensation problems may also arise in the feed lines. On the whole, such a calibration process is technically rather complicated, because precise controls and heating means are necessary, which make the design of the instruments technically more complicated and, as a result, also more expensive.

SUMMARY AND OBJECTS OF THE INVENTION

The object of the present invention is to provide a simpler and more favorable process for calibrating breath alcohol-measuring instruments as well as a combination of a calibrating gas generator and a breath alcohol-measuring instrument for carrying out the process.

According to the invention, a process is provided for calibrating a breath alcohol-measuring instrument by means of a calibrating gas generator with a liquid container for aqueous ethanol solution and air feed means. The means is designed for allowing air to bubble through the ethanol solution and for sending gas from the atmosphere above the ethanol solution to the said breath alcohol-measuring instrument. The process includes the steps of:

measuring the temperature of the ethanol solution with a thermometer;

generating an electric signal representing the temperature;

receiving the electric signal in a transmission means and passing on the electric signal or a conditioned signal prepared from the electric signal to a breath alcohol-measuring instrument and into an electronic evaluating unit;

automatically converting the measurement result obtained by the breath alcohol-measuring instrument in the electronic evaluating unit to a measurement result to be expected at a preset reference temperature by means of a preset dependence on the temperature of the aqueous ethanol solution obtained from the electric signal or from the processed signal and on the preset reference temperature; and evaluating the measurement result expected at the preset reference temperature for calibrating the breath alcohol-measuring instrument.

The invention also provides a combination of a breath alcohol-measuring instrument and a calibrating gas generator for carrying out the process. The combination includes the thermometer arranged in a liquid container of a calibrating gas generator and the transmission means is arranged at the liquid container. A cable connects the transmission means to an interface at the breath alcohol-measuring instrument in order to pass on the electric signal representing the temperature into the electronic evaluating unit of the breath alcohol-measuring instrument. The electronic evaluating unit is set up so as to convert the measurement result obtained for the ethanol concentration to the measurement result to be expected at a preset reference temperature by means of a preset dependence on the temperature of the aqueous ethanol solution, which is obtained from the electric signal or from the processed signal, and on the preset reference temperature.

The present invention provides that the temperature of the ethanol solution is measured in the calibrating gas generator, and an electric signal representing the temperature is generated, and this signal is sent after processing to the breath alcohol-measuring instrument via a transmission means and further into the electronic evaluating unit in the breath alcohol-measuring instrument. The electronic evaluating unit is set up such that the electric signal representing the temperature is used to convert the measurement result into the measurement result to be expected at a preset reference temperature in the electronic evaluating unit. The measurement result thus obtained at the reference temperature can then be used for the calibration as usual, because this measurement result at the reference temperature depends only on the ethanol concentration in the aqueous solution, which is assumed to be known.

The above-described temperature dependence can be rewritten for conversion to the measurement result to be expected at the reference temperature:

$$M_{ref} = M_0 \cdot e^{-a(T-34° C.)}$$

in which $M_0$ is the actual measurement result, which is determined in the electronic evaluating unit at the actual temperature T. Consequently, the actual measurement result can be converted by means of the above equation to the measured signal $M_{ref}$ to be expected at the reference temperature of $T_{ref} = 34°$ C.

The electronic evaluating unit of the breath alcohol-measuring instrument can be adapted in a relatively simple manner in order to perform the necessary conversion functions, because the electronic evaluating unit is made in the form of chips anyway, which can be easily expanded or programmed such as to be able to perform the desired conversion functions. However, an interface, in which the electric signal representing the temperature can be fed in from the transmission means, must be provided at the breath alcohol-measuring instrument. Furthermore, the breath alcohol-measuring instrument must be provided with a switching means, with which a switchover between calibration mode and measurement mode can be performed, the electronic evaluating unit performing the conversion described in the calibration mode only.

The conversion of the electric signal of the thermometer into a digital signal may be performed either already in the transmission means or only behind the interface in the breath alcohol-measuring instrument.

The process according to the present invention offers considerable advantages, because thermostatting of the calibrating gas generator is no longer necessary.

A calibrating gas generator-breath alcohol-measuring instrument combination for carrying out the process may have a calibrating gas generator with a liquid container, in which the thermometer is stationarily arranged and is permanently connected to the transmission means, wherein the transmission means is also provided with a cable that can be connected to an interface at the breath alcohol-measuring instrument in order to forward the electric signal representing the temperature into the electronic evaluating unit of the breath alcohol-measuring instrument. The electronic evaluating unit is set up such as to convert the measurement result obtained for the ethanol concentration in the gas phase to the measurement result to be expected at a preset reference temperature by means of a preset dependence on the temperature of the aqueous ethanol solution, which is obtained from the electric signal or from the processed signal, and on the preset reference temperature.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The figure schematically shows the design of a combination of calibrating gas generator and breath alcohol-measuring instrument for carrying out the process according to the present invention.

DESCRIPTION OF THE PREFERRED EMBODIMENT

Referring to the drawing in particular, the invention comprises a calibrating gas generator 1 which has a liquid container 2, which is partially filled with aqueous ethanol solution. The air feed means, namely, a pump 15, a feed line 4, a bubbling body 5, and a discharge line 6 to the breath alcohol-measuring instrument 7, are used to allow air to bubble through the aqueous ethanol solution and to subsequently pass on the air saturated with ethanol and water vapor to the measuring input of the breath alcohol-measuring instrument 7. The bubbling body 5 generates the finest possible bubbles having a large overall surface in order to achieve a good mass exchange, so that a state of equilibrium with the solution is reached during the flow.

A thermometer 8, which generates an electric signal representing the temperature of the solution and passes it on to a transmission means 9, dips into the aqueous ethanol solution in the liquid container 2. The electric signal is passed on by the transmission means 9 to an interface at the breath alcohol-measuring instrument 7 either directly or after processing or conversion, via a cable. The cable and the transmission means 9 form a transmission arrangement. The interface is connected to the electronic evaluating unit of the breath alcohol-measuring instrument. In typical cases, the electronic evaluating unit is set up in the form of a microprocessor, which may be programmed by corresponding preparation for the further evaluation of the temperature signal. The actual temperature value is obtained from the signal representing the temperature and is used in the electronic evaluating unit to convert the measurement result obtained for the alcohol concentration into the measurement result $M_{ref}$ to be expected at the preset reference temperature. The reference temperature is, e.g., 34° C., so that the conversion to the reference measurement result $M_{Ref}$ can be performed in the electronic evaluating unit with the following formula:

$$M_{ref} = M_0 \cdot e^{-a(T-34° C.)}.$$

The measurement result thus obtained for the ethanol concentration in the gas phase at the reference temperature can then be used directly for the calibration in the case of known concentration of the ethanol solution, without thermostatting being necessary.

The transmission means 9 is operated with a battery to eliminate the need for connection to the power line. To achieve the longest possible operating time without changing the battery, the transmission means 9 is switched on only when a manometric switch 11 senses flow through the calibrating gas generator 1. The transmission means 9 will then be switched on by a switching-on means 10.

The transmission means 9 can pass on the analog signal supplied by the thermometer 8 either in the analog form or it may already perform a conversion into a digital signal.

While specific embodiments of the invention have been shown and described in detail to illustrate the application of the principles of the invention, it will be understood that the invention may be embodied otherwise without departing from such principles.

What is claimed is:

1. A process for calibrating a breath alcohol-measuring instrument with a calibrating gas generator with a liquid container containing an aqueous ethanol solution and an air feed for allowing air to bubble through the ethanol solution creating saturated air and for sending the saturated air from the atmosphere above the ethanol solution to the breath alcohol-measuring instrument, the process comprising the steps of:

measuring the temperature of the ethanol solution with a thermometer;

generating an electric signal representing the temperature measured;

receiving the electric signal in a transmission means and passing on the electric signal or a conditioned signal prepared from the electric signal to the breath alcohol-measuring instrument and into an electronic evaluating unit;

automatically converting a measurement result obtained by the breath alcohol-measuring instrument in the electronic evaluating unit to a measurement result to be expected at a preset reference temperature by means of a preset dependence on the temperature of the aqueous ethanol solution obtained from the electric signal or from the conditioned signal and on the preset reference temperature; and evaluating the measurement result expected at the preset reference temperature to calibrate the breath alcohol-measuring instrument.

2. The process in accordance with claim 1, in which the transmission means is supplied with power from a battery.

3. The process in accordance claim 1, wherein a switching-on means is provided which switches on the transmission means only when it is determined via a manometric switch that air is flowing through the air feed to the breath alcohol-measuring instrument.

4. The process in accordance with claim 1, wherein signal-processing circuits in the transmission means convert the electric signal of the thermometer representing the temperature measured into a digital signal.

5. A breath alcohol-measuring instrument and a calibrating gas generator combination, comprising:

a breath alcohol-measuring instrument with an interface and with an electronic evaluating unit;

a liquid container for containing a liquid;

a thermometer arranged in said liquid container;

a transmission means arranged adjacent to said liquid container;

a cable connecting said transmission means to said interface of said breath alcohol-measuring instrument in order to pass on an electric signal representing the temperature of the liquid contained within the liquid container into said electronic evaluating unit of the said breath alcohol-measuring instrument; and means associated with said electronic evaluating unit to convert a measurement result obtained for an ethanol concentration at the temperature sensed by said thermometer to a measurement result to be expected at a preset reference temperature by means of a preset dependence on the temperature of liquid, which is obtained from the electric signal or from a processed signal, and on the preset reference temperature.

6. The combination in accordance with claim 5, wherein said transmission means is provided with a battery supplying power.

7. The combination in accordance with claim 5, further comprising:

an air feed for allowing air to bubble through the liquid creating saturated air and for sending the saturated air from the atmosphere above the ethanol solution to the breath alcohol-measuring instrument;

switching-on means; and a manometric switch which sends an electric signal to said switching-on means when the air feed is operating, said manometric switch being provided in said liquid container, wherein said switching-on means is designed for maintaining said transmission means switched on as long as said air feed is operating according to the indication of said manometric switch.

8. A process for calibrating a breath alcohol-measuring instrument with a calibrating gas generator with a liquid container containing an aqueous ethanol solution and an air feed for allowing air to bubble through the ethanol solution creating saturated air and for sending the saturated air from the atmosphere above the ethanol solution to the breath alcohol-measuring instrument, the saturated gas having a known ethanol concentration at a preset reference temperature, the process comprising the steps of:

measuring the temperature of the ethanol solution with a thermometer;

generating an electric signal representing the temperature;

passing on the electric signal or a conditioned signal prepared from the electric signal to an electronic evaluating unit of the breath alcohol-measuring instrument measuring the ethanol concentration of the saturated gas using the breath alcohol-measuring instrument to obtain an actual measurement result;

converting the actual measurement result obtained by the breath alcohol-measuring instrument in the electronic evaluating unit to obtain a corresponding measurement result for the preset reference temperature based on a preset dependence on the temperature of the aqueous ethanol solution obtained and on the preset reference temperature; and calibrating the breath alcohol-measuring instrument based on the corresponding measurement result and the known ethanol concentration at the preset reference temperature.

9. The process in accordance with claim 8, wherein the step of passing on the electric signal includes receiving the electric signal in a transmission device and passing on the electric signal or a conditioned signal prepared from the electric signal from the transmission device to the electronic evaluating unit wherein the transmission device is supplied with power from a battery.

10. The process in accordance with claim 9, wherein a switch is used to switch on the transmission device only when it is determined via a manometric switch that air is flowing through the air feed to the breath alcohol-measuring instrument.

11. The process in accordance with claim 9, wherein signal-processing circuits in the transmission device convert the electric signal of the thermometer representing the temperature into a digital signal.

12. A breath alcohol-measuring instrument and a calibrating gas generator combination, comprising:

a breath alcohol-measuring instrument with an interface and with an electronic evaluating unit;

a liquid container with an ethanol solution therein;

a thermometer arranged in said liquid container;

an air feed for allowing air to bubble through the ethanol solution creating saturated air and for sending from the atmosphere above the ethanol solution to said breath alcohol-measuring instrument, the saturated air having a known ethanol concentration at a preset reference temperature;

a transmission arrangement connected to said thermometer and connected to said breath alcohol-measuring instrument to pass on an electric signal representing the temperature to said electronic evaluating unit; and a conversion means associated with said electronic evaluating unit to convert an actual ethanol concentration measurement at the temperature sensed by said thermometer to a corresponding measurement result based on a preset dependence on the temperature of the aqueous ethanol solution obtained and on the preset reference temperature.

13. The combination in accordance with claim 12, wherein said transmission arrangement is provided with a battery supplying power.

14. The combination in accordance with claim 12, further comprising:

switching-on means; and a manometric switch which sends an electric signal to said switching-on means when the air feed is operating, said manometric switch being provided in said liquid container, wherein said switching-on means is designed for maintaining said transmission arrangement switched on as long as said air feed is operating according to the indication of said manometric switch.

* * * * *